(12) United States Patent
Nakaoka et al.

(10) Patent No.: US 7,518,022 B2
(45) Date of Patent: Apr. 14, 2009

(54) LIQUID VEGETABLE UNSATURATED ALCOHOL AND PROCESS FOR PRODUCING THE SAME

(75) Inventors: Hisao Nakaoka, Uji (JP); Mamoru Mototani, Kyoto (JP)

(73) Assignee: New Japan Chemical Co., Ltd., Kyoto-Shi (JP)

( * ) Notice: Subject to any disclaimer, the term of this patent is extended or adjusted under 35 U.S.C. 154(b) by 673 days.

(21) Appl. No.: 10/508,956

(22) PCT Filed: Apr. 17, 2003

(86) PCT No.: PCT/JP03/04878

§ 371 (c)(1),
(2), (4) Date: Oct. 5, 2004

(87) PCT Pub. No.: WO03/089393

PCT Pub. Date: Oct. 30, 2003

(65) Prior Publication Data

US 2005/0152929 A1 Jul. 14, 2005

(30) Foreign Application Priority Data

| Apr. 19, 2002 | (JP) | ................. 2002-118189 |
| Feb. 27, 2003 | (JP) | ................. 2003-050903 |
| Apr. 15, 2003 | (JP) | ................. 2003-109726 |

(51) Int. Cl.
*C07C 27/04* (2006.01)
*C07C 69/02* (2006.01)

(52) U.S. Cl. .................. 568/885; 568/884; 568/881; 568/876; 554/174; 554/230

(58) Field of Classification Search ................. 554/167, 554/174, 230; 568/881, 884, 885, 876
See application file for complete search history.

(56) References Cited

U.S. PATENT DOCUMENTS

| 5,276,204 | A | * | 1/1994 | Schmid et al. .............. 568/616 |
| 5,672,781 | A | * | 9/1997 | Koehler et al. .............. 568/885 |
| 5,917,097 | A | * | 6/1999 | Koehler et al. .............. 568/884 |
| 6,187,974 | B1 | * | 2/2001 | Wieczorek et al. .......... 568/885 |
| 6,229,056 | B1 | | 5/2001 | Ansmann et al. |
| 2002/0035159 | A1 | * | 3/2002 | Heck et al. .................. 514/739 |
| 2002/0037932 | A1 | * | 3/2002 | Heck et al. .................. 514/724 |

FOREIGN PATENT DOCUMENTS

| JP | 61-157589 | | 7/1986 |
| JP | 61-178912 | | 8/1986 |
| JP | 62-234536 | | 10/1987 |
| JP | 1002-089403 | * | 4/2001 |
| JP | 2001-89403 | | 4/2001 |

OTHER PUBLICATIONS

International Search Report for corresponding international application No. PCT/JP03/04878 dated Jul. 22, 2003.
International Preliminary Examination Report for corresponding international application No. PCT/JP03/04878 dated May 11, 2004.
The Supplementary European Search Report for corresponding European patent application No. 03717617, dated May 9, 2006. (Citing References AA, AB and AF-AH.).

* cited by examiner

*Primary Examiner*—Daniel M Sullivan
*Assistant Examiner*—Yate' K Cutliff
(74) *Attorney, Agent, or Firm*—Kratz, Quintos & Hanson, LLP

(57) ABSTRACT

The invention is directed to liquid vegetable unsaturated alcohol mixture having an iodine value of 88 to 100 and a cloud point less than 7° C., the unsaturated alcohol mixture being prepared by reduction of a vegetable unsaturated fatty acid mixture and/or an alkyl ester thereof in the presence of a zinc-type catalyst having a copper content of 30 ppm or less, the vegetable unsaturated fatty acid mixture being prepared from at least one vegetable oil selected from the group consisting of palm oil, coconut oil and palm kernel oil. The invention also concerns a liquid vegetable unsaturated alcohol mixture having an iodine value of 88 to 100, a cloud point less than 7° C. or lower and a conjugated diene content of 1 wt. % or less.

7 Claims, No Drawings

LIQUID VEGETABLE UNSATURATED ALCOHOL AND PROCESS FOR PRODUCING THE SAME

FIELD OF THE INVENTION

The present invention relates to liquid vegetable unsaturated alcohol mixture and a process for preparing the same, and more particularly to high-quality liquid vegetable unsaturated alcohol mixture suitable as a raw material for cosmetics and a process for preparing the same.

BACKGROUND ART

Unsaturated alcohols, typically oleyl alcohol, are compounds which are useful in themselves or as alkylene oxide adducts in the production of cosmetics, textile oil and so on.

In the prior art, such unsaturated alcohols have been conventionally produced from wax obtained from sperm whales by saponification or sodium metal reduction. After a law prohibited the catching of sperm whales, a method was proposed for producing unsaturated alcohols by ester reduction of unsaturated fatty acids prepared from triglycerides of unsaturated fatty acids such as beef tallow, pork tallow or the like, and/or methyl esters thereof. This is the method that has been mainly carried out since then.

In view of the recent BSE(Bovine Spongiform Encephalopathy) problem, attention has been increasingly focused on unsaturated alcohols prepared from vegetable fats and oils. In recent years, especially there has been a great demand for unsaturated alcohols prepared from vegetable fats and oils for use as materials in cosmetics including skin lotions, skin creams, shampoos, hair rinses, hair treatments and the like which are applied to the human body or hair. Further, attention is being paid to vegetable unsaturated alcohols as raw materials for cosmetics since the public image of a product produced from vegetable raw materials is favorable.

Unsaturated alcohols are used especially because of their retention of liquidity. Because turbidity and cloudiness of a liquid exceedingly impair its commercial value, a cosmetic product would not be qualified as a liquid cosmetic if it becomes turbid or solids precipitate at about 10° C. in the room of a Japanese house in winter without an air conditioner.

If a liquid product has too high a cloud point, small quantities of components in the product are likely to become crystalline, and the product easily becomes cloudy or turbid during storage. For example, a liquid product is partly crystallized in a drum or the like, and crystals precipitate, resulting in a tendency to change part of the formulation. Consequently when a liquid product lacks a low cloud point for practical use, it may lead to serious problems.

Unsaturated alcohols for use as a material for cosmetics are required to be stable to light and to be unvaried in color in the long term.

Furthermore, when an unsaturated alcohol is used as an alkylene oxide adduct, it needs to be resistant to being colored in the presence of any potassium hydroxide used as a catalyst. Moreover, when an unsaturated alcohol is used to esterify a saturated or unsaturated fatty acid, lactic acid, phosphoric acid or the like, the ester is required to be resistant to being colored in the presence of any p-toluenesulfonic acid or sulfuric acid used as a catalyst. In addition, when an unsaturated alcohol is used in a sulfuric acid ester salt, the sulfuric acid ester salt is required to be resistant to being colored in the presence of any chlorosulfonic acid, acidic $SO_3$ gas or acidic sulfuric acid ester before neutralization.

When liquid vegetable unsaturated alcohols are used as a raw material for a derivative in cosmetics, they must be stable to coloring in the presence of acidic or basic substances.

An unsaturated alcohol used as a material for cosmetics is required to give off little or no odor. Furthermore, cosmetic products containing such unsaturated alcohols must not vary in smell nor take a prolonged time to emit their smell.

For example, the following documents disclose liquid vegetable unsaturated alcohol products and processes for preparing them.

(1) Japanese Unexamined Patent Publication (PCT) No. 1997-504013 (page 6, lines 23 to 26; Examples 1 to 3, and elsewhere) discloses a vegetable unsaturated alcohol mixture having an iodine value of 20 to 110 and a process for preparing the same using a $CuCrO_4$ catalyst. The publication describes that the obtained vegetable unsaturated alcohol mixture is an unsaturated aliphatic alcohol mixture that is stable to oxidation and exhibits a preferred low-temperature behavior. The document mentions that unsaturated aliphatic alcohol mixture containing 4.5% or less of conjugated dienes are excellent in terms of stability to oxidation. The document sets forth a working example wherein an unsaturated aliphatic alcohol mixture having an iodine value of 73.9, a conjugated diene content of 3.2%, and a softening point of 22.9° C. was prepared using a $CuCrO_4$ catalyst.

The words "a preferred low-temperature behavior" used in the document shows that the softening point is low. Since the softening point is a temperature at which a solid partly starts to melt and becomes soft while it is heated, such low-temperature behavior is said to be due to the melting point of the main component in the solid.

(2) Japanese. Unexamined Patent Publication (PCT) No. 1998-502654 (page 9, line 24 to page 10, line 6; page 12, lines 8 to 9; Table 3, and elsewhere) discloses a vegetable unsaturated alcohol having an iodine value of 85 to 100 which is prepared from a laurin oil-derived unsaturated fatty acid, and a process for preparing the same by a fixed bed reactor of Cu/Cr/Zn or Cu/Cr/Cd mixed oxide-type or in a trickle phase of a silica gel-supported catalyst containing 20 to 40% by weight of copper chromite. The document also sets out that the obtained vegetable unsaturated alcohol is stable to oxidation and exhibits a preferred low-temperature behavior.

The term "preferred low-temperature behavior" used in the document denotes that the solidifying point is low. More specifically, the solidifying point is a temperature at which a liquid starts to solidify as a whole while the liquid is cooled. Thus, the document shows that such low-temperature behavior is due to the melting point of the main component in the liquid.

The solidifying point or softening point of unsaturated alcohols can be relatively easily controlled by selecting the type of main components. On the other hand, however, it is very difficult to control the production of small quantities of crystalline components which are responsible for the increase in the cloud point of unsaturated alcohols in the prior art process for preparing unsaturated alcohols, especially in those prior art processes using a hydrogenation catalyst. This problem has not yet been satisfactorily overcome.

Japanese Unexamined Patent Publications (PCT) No. 1997-504013 and No. 1998-502654 entirely lack disclosure color stability in the presence of an acidic or basic substance and long-term coloring resistance to light.

(3) Japanese Unexamined Patent Publication No. 2001-89403 (claim 1, paragraph 0040, Table 1 on page 5, and elsewhere) discloses a process for preparing an unsaturated alcohol by hydrogenation of an unsaturated fatty acid or an ester thereof using a zinc-chrome oxide catalyst or a zinc-chrome-aluminum oxide catalyst containing 100 ppm or less of copper and 200 ppm or less of nickel calculated on a metal basis. Further, the publication describes a working example in which an unsaturated alcohol mixture having an iodine value of about 92 and a cloud point of 0.5 to 2.1° C. was prepared by hydrogenation of an industrial unsaturated fatty acid using a zinc-type catalyst having a copper content of 15 to 20 ppm and a nickel content of 20 to 60 ppm.

Unsaturated fatty acids for industrial use are usually prepared from animal fats and oils as starting materials. Unsaturated fatty acids and unsaturated alcohols prepared from animal fats and oils as starting materials are generally unlikely to induce cloudiness at a low temperature. Although the reason for this phenomenon is unknown, it is presumable that fatty acids derived from animal fats and oils include fatty acids having an odd number of carbon atoms, and the finally obtained unsaturated alcohols comprise numerous components.

On the other hand, unsaturated fatty acids derived from vegetable fats and oils only have an even-number of carbon atoms. Consequently it is difficult to provide an unsaturated alcohol end-product which is unlikely to cause cloudiness at low temperatures.

DISCLOSURE OF THE INVENTION

The first object of the present invention is to provide a liquid vegetable unsaturated alcohol mixture which has excellent retention of liquidity and is unlikely to become cloudy on change of temperature, and a process for preparing the same.

The second object of the present invention is to provide a liquid vegetable unsaturated alcohol mixture which has excellent retention of liquidity, is unlikely to become cloudy on change of temperature, and has outstanding long-term light resistance to coloring and color stability in the presence of acids or bases, and a process for preparing the same.

The present inventors conducted extensive research to achieve the foregoing objects and found the following.

(1) if even a small amount of a component having a high crystallization temperature is present in a liquid unsaturated alcohol mixture, part of the component becomes crystalline and causes cloudiness as the temperature is lowered. Therefore the cloud point of a liquid unsaturated alcohol mixture is important as an index for cloudiness with changing temperatures. Liquid unsaturated alcohol mixture having an iodine value of 88 to 100 and a cloud point of less than 7° C. can maintain their liquid state over a relatively broad temperature range, and clouding of the liquid with change of temperature is scarcely or not at all observable in such an unsaturated alcohol mixture.

(2) A zinc-type catalyst with a copper content of 30 ppm or less can be effectively used for reduction in order to prepare an unsaturated alcohol mixture having a cloud point of less than 7° C. without lowering the iodine value (i.e., suppressing the conversion of unsaturated alcohols to saturated alcohols) by reducing a vegetable unsaturated fatty acid or ester thereof prepared from vegetable oil.

(3) A Liquid vegetable unsaturated alcohol mixture, due to decreased content of conjugated dienes to zero or to 1 wt. % or less, and especially 0.5 wt. % or less, shows an improved color stability in the presence of an acidic or basic substance and enhanced long-term stability to light.

(4) When a liquid vegetable unsaturated alcohol mixture is slightly hydrogenated, the conjugated diene content of the unsaturated alcohol mixture can be lowered without decreasing the iodine value and increasing the cloud point. In contrast, the prior art methods of lowering the conjugated diene content by elevating the temperature during ester reduction are likely to lower the iodine value by conversion of unsaturated alcohols to saturated alcohols and tend to increase the cloud point as the conjugated diene content decreases.

The invention was completed based on the foregoing novel findings and provides the following liquid vegetable unsaturated alcohol mixtures and the processes for preparing the same.

1. A liquid vegetable unsaturated alcohol mixture having an iodine value of 88 to 100 and a cloud point of less than 7° C., the unsaturated alcohol mixture being prepared by reduction of a vegetable unsaturated fatty acid mixture and/or an alkyl ester thereof in the presence of a zinc-type catalyst having a copper content of 30 ppm or less, the vegetable unsaturated fatty acid mixture being prepared from at least one vegetable oil selected from the group consisting of palm oil, coconut oil and palm kernel oil.

2. The liquid vegetable unsaturated alcohol mixture of item 1 used in a material for cosmetics.

3. Use of the liquid vegetable unsaturated alcohol mixture of item 1 as a material for cosmetics.

4. A derivative of the liquid vegetable unsaturated alcohol mixture of item 1.

5. The derivative of the liquid vegetable unsaturated alcohol mixture of item 4 which is any one of the following:

(a) an alkylene oxide adduct of the liquid vegetable unsaturated alcohol mixture;

(b) a sodium salt, a potassium salt, a triethanolamine salt or an ammonium salt of a sulfuric acid ester of the liquid vegetable unsaturated alcohol mixture or an alkylene oxide adduct thereof;

(c) carboxylic acid ether of the liquid vegetable unsaturated alcohol mixture or an alkylene oxide adduct thereof, or a sodium salt, a potassium salt, a triethanolamine salt or an ammonium salt of the carboxylic acid ether;

(d) an ester of the liquid vegetable unsaturated alcohol mixture with an acid selected from the group consisting of fatty acids and lactic acid; and (e) phosphate ester of the liquid vegetable unsaturated alcohol mixture or alkylene oxide adduct thereof, or a sodium salt, a potassium salt, a triethanolamine salt or an ammonium salt of the ester.

6. A derivative of the liquid vegetable unsaturated alcohol mixture of item 4 used as a material for cosmetics.

7. Use of the derivative of the liquid vegetable unsaturated alcohol mixture of item 4 as a material for cosmetics.

8. A liquid vegetable unsaturated alcohol mixture having an iodine value of 88 to 100, a cloud point of lower than 7° C. and a conjugated diene compound content of 1 wt. % or less.

9. The liquid vegetable unsaturated alcohol mixture according to item 8, wherein the content of volatile components is 500 ppm or less as measured by head space gas chromatography when the alcohol mixture is heated at 150° C. for 10 minutes.

10. The liquid vegetable unsaturated alcohol mixture of item 8 used in a material for cosmetics.

11. Use of the liquid vegetable unsaturated alcohol mixture of item 8 as a material for cosmetics.

12. A derivative of the liquid vegetable unsaturated alcohol mixture of item 8.

13. The derivative of the liquid vegetable unsaturated alcohol mixture of item 12 which is any one of the following:
 (a) an alkylene oxide adduct of the liquid vegetable unsaturated alcohol mixture;
 (b) a sodium salt, a potassium salt, a triethanolamine salt or an ammonium salt of a sulfuric acid ester of the liquid vegetable unsaturated alcohol mixture or an alkylene oxide adduct thereof;
 (c) an ether carboxylic acid of the liquid vegetable unsaturated alcohol mixture or an alkylene oxide adduct thereof, or a sodium salt, a potassium salt, a triethanolamine salt or an ammonium salt of such an ether carboxylic acid;
 (d) an ester of the liquid vegetable unsaturated alcohol mixture with an acid selected from the group consisting of fatty acids and lactic acid; and
 (e) phosphoric acid ester of the liquid vegetable unsaturated alcohol mixture or an alkylene oxide adduct thereof, or a sodium salt, a potassium salt, a triethanolamine salt or an ammonium salt of the ester.

14. The derivative of the liquid vegetable unsaturated alcohol mixture of item 12 used as a material for cosmetics.

15. Use of the derivative of the liquid vegetable unsaturated alcohol mixture of item 12 as a material for cosmetics.

16. A liquid vegetable unsaturated alcohol mixture obtained by reduction of a vegetable unsaturated fatty acid and/or an alkyl ester thereof in the presence of a zinc-type catalyst having a copper content of 30 ppm or less, the vegetable unsaturated fatty acid mixture being prepared from at least one vegetable oil selected from the group consisting of palm oil, coconut oil and palm kernel oil.

17. The liquid vegetable unsaturated alcohol mixture according to item 16, wherein the zinc-type catalyst is at least one catalyst selected from the group consisting of zinc-chrome oxide, zinc-aluminum oxide, zinc-aluminum-chrome oxide, zinc-chrome-manganese oxide, zinc-iron oxide and zinc-iron-aluminum oxide.

18. A liquid vegetable unsaturated alcohol mixture according to item 16 that is prepared by slight hydrogenation of the obtained liquid vegetable unsaturated alcohol mixture.

19. The liquid vegetable unsaturated alcohol mixture according to item 18, wherein the slight hydrogenation is carried out using a copper-containing catalyst.

20. The liquid vegetable unsaturated alcohol mixture according to item 18, wherein the slight hydrogenation is carried out at a hydrogen pressure within the range of from 1 MPa to atmospheric pressure, and a temperature at 50 to 200° C.

21. The liquid vegetable unsaturated alcohol mixture according to item 16 which is prepared by deodorizing the obtained liquid vegetable unsaturated alcohol mixture.

22. The liquid vegetable unsaturated alcohol mixture according to item 21, wherein the deodorization is carried out by steam at 100 to 200° C., and 0.1 to 70 KPa with a steam blowing amount of 0.1 to 20 wt. %.

23. The liquid vegetable unsaturated alcohol mixture according to item 16 which is prepared by a process including a distillation step.

24. The liquid vegetable unsaturated alcohol mixture of item 16 used as a material for cosmetics.

25. Use of the liquid vegetable unsaturated alcohol mixture of item 16 as a material for cosmetics.

26. A derivative of the liquid vegetable unsaturated alcohol mixture of item 16.

27. The derivative of the liquid vegetable unsaturated alcohol mixture of item 26 which is any one of the following:
 (a) an alkylene oxide adduct of the liquid vegetable unsaturated alcohol mixture;
 (b) a sodium salt, a potassium salt, a triethanolamine salt or an ammonium salt of a sulfuric acid ester of the liquid vegetable unsaturated alcohol mixture or an alkylene oxide adduct thereof;
 (c) an ether carboxylic acid of the liquid vegetable unsaturated alcohol mixture or an alkylene oxide adduct thereof, or a sodium salt, a potassium salt, a triethanolamine salt or an ammonium salt of such an ether carboxylic acid;
 (d) an ester of the liquid vegetable unsaturated alcohol mixture with an acid selected from the group consisting of fatty acids and lactic acid; and
 (e) phosphoric acid ester of the liquid vegetable unsaturated alcohol mixture or an alkylene oxide adduct thereof, or a sodium salt, a potassium salt, a triethanolamine salt or an ammonium salt of the ester.

28. The derivative of the liquid vegetable unsaturated alcohol mixture of item 26 used as a material for cosmetics.

29. Use of the derivative of the liquid vegetable unsaturated alcohol mixture of item 26 as a material for cosmetics.

30. A process for preparing a liquid vegetable unsaturated alcohol mixture, the process comprising the step of reducing a vegetable unsaturated fatty acid mixture and/or an alkyl ester thereof in the presence of a zin-type catalyst having a copper content of 30 ppm or less, the vegetable unsaturated fatty acid mixture being prepared from at least one vegetable oil selected from the group consisting of palm oil, coconut oil and palm kernel oil.

31. The process according to item 30, wherein the zinc type catalyst is at least one catalyst selected from the group consisting of zinc-chrome oxide, zinc-aluminum oxide, zinc-aluminum-chrome oxide, zinc-chrome-manganese oxide, zinc-iron oxide and zinc-iron-aluminum oxide.

32. The process according to item 30 which includes a step of slightly hydrogenating the obtained liquid vegetable unsaturated alcohol mixture.

33. The process according to item 32, wherein the slight hydrogenation is carried out using a copper-containing catalyst.

34. The process according to item 32, wherein the slight hydrogenation is carried out at a hydrogen pressure within the range of from 1 MPa to atmospheric pressure, and a temperature at 50 to 200° C.

35. The process according to item 30 which includes a step of deodorizing the obtained liquid vegetable unsaturated alcohol mixture.

36. The process according to item 35, wherein the deodorization is conducted by steam at 100 to 200° C., and 0.1 to 70 KPa with a steam blowing amount of 0.1 to 20 wt. %.

37. The process according to item 30 which includes a step of distillation.

According to the invention, there is provided a liquid vegetable unsaturated alcohol mixture which is superior in retention of liquidity and is unlikely to become cloudy with a change of temperature, and a process for preparing the same. According to the invention, there is also provided a liquid vegetable unsaturated alcohol mixture which is superior in retention of liquidity, unlikely to become cloudy with a change of temperature, and outstanding in long-term light resistance to coloring and in color stability in the presence of acids or bases, and a process for preparing the same.

DETAILED DESCRIPTION OF THE INVENTION

The present invention is described below in greater detail. A description of the production process of the invention is given first and then the liquid vegetable unsaturated alcohol mixture of the invention prepared by the production process.

(1) Process for Preparing Liquid Vegetable Unsaturated Alcohol Mixture

Basic Construction

The process for preparing a liquid vegetable unsaturated alcohol mixture according to the invention comprises the step of reducing a vegetable unsaturated fatty acid mixture and/or an alkyl ester thereof in the presence of a zinc-type catalyst having a copper content of 30 ppm or less, the vegetable unsaturated fatty acid mixture being prepared from at least one vegetable oil selected from the group consisting of palm oil, coconut oil and palm kernel oil. The process of the invention is characterized by this step.

Raw Material

As described above, the oil for preparing the vegetable unsaturated fatty acid mixture is at least one vegetable oil selected from the group consisting of palm oil, coconut oil and palm kernel oil. Palm oleic oil or palm stearic oil prepared by solid fractionation by cooling of palm oil or the like as described later can be suitably used.

These fats and oils are alcohol raw materials which are available as fresh seeds since these oil crops are grown year-round on large-scale plantations in Southeast Asia. These alcohol raw material fats and oils can be easily supplied in the required quantity. Further, these materials are inexpensive and are readily available since oil mill factories are generally installed in the vicinity of the cultivation area and high-quality fats and oils are produced regularly.

An unsaturated fatty acid prepared from palm oil, coconut oil or palm kernel oil contains a small amount of linoleic acid which is responsible for a decrease in oxidation stability and in color stability. This feature is advantageous in producing an unsaturated alcohol mixture having an iodine value of about 88 to about 100 and a cloud point of less than 7° C., and preferably a conjugated diene compound content of 1 wt. % or less.

In contrast, linoleic acid is contained in a large amount in unsaturated fatty acids prepared from the soybean oil and linseed oil hitherto used as raw materials for vegetable unsaturated alcohols. Linoleic acid is a compound which serves as a source capable of producing conjugated diene compounds. For example, when soybean or linseed oil is used as the raw material, and reduction is conducted using a zinc-type catalyst according to the process of the invention, an unsaturated alcohol mixture having an iodine value (about 110 to about 130) far greater than the unsaturated alcohol mixture of the invention (an iodine value of about 88 to about 100) is produced, it also contains a large amount of conjugated dienes (about 15 wt. %).

Even if the raw material oil contains a large amount of linoleic acid, an unsaturated alcohol mixture having an iodine value of about 88 to about 100 can be produced by reduction at a higher reaction temperature than the process of the invention, but the obtained unsaturated alcohol mixture has a high cloud point and an unsaturated alcohol mixture having a low cloud point below 7° C. as in the present invention can not be produced.

Palm oil, coconut oil and palm kernel oil can be produced by squeezing fresh seeds as described above. Thus, the fatty acid useful as the raw material is not deteriorated by oxidation, whereby a high-quality unsaturated alcohol mixture having a high color stability is produced. In contrast, unsaturated alcohols mixture of high color stability can not be produced from fatty acids or alkyl esters thereof obtained from used vegetable oils (e.g., recovered frying oil).

However, unsaturated alcohol products with liquidity retention sufficient for practical use have not been manufactured from palm oil, coconut oil, or palm kernel oil.

The vegetable unsaturated fatty acid is produced by hydrolyzing at least one of the vegetable oils selected from the group consisting of palm oil, coconut oil and palm kernel oil. The obtained vegetable unsaturated fatty acid can be used as a material to be subjected to reduction reaction. Optionally the vegetable unsaturated fatty acid may be esterified with an alcohol, or ester exchange reaction may be effected between a vegetable oil and an alcohol, whereby an alkyl ester of the vegetable unsaturated fatty acid is produced. The obtained alkyl ester may be used as the material to be subjected to reduction reaction. An alkyl ester is more preferable than the vegetable unsaturated fatty acid. Examples of the alcohol are alcohols having 1 to 4 carbon atoms, and preferably methyl alcohol which allows efficient ester reduction.

The vegetable unsaturated fatty acid thus obtained and/or alkyl ester thereof can be used as is, i.e. as the material to be reduced. Preferred are those prepared by distillation for concentrating the components having 16 to 18 carbon atoms or especially the components having 18 carbon atoms.

When required, it is desirable to use an unsaturated fatty acid or alkyl ester thereof having an iodine value of about 75 to about 100, especially about 80 to about 100, further especially about 85 to about 95, calculated as the methyl ester, which can be prepared by distillation and solid fractionation by cooling.

It is desirable to use an unsaturated fatty acid mixture and/or alkyl ester thereof having a high oleic acid content that is prepared by distillation and/or solid fractionation by cooling. For example, an unsaturated fatty acid mixture with an iodine value of about 85 to about 95 prepared by hydrolysis of palm kernel oil, distillation and then solid fractionation by cooling is preferred because of its high oleic acid content and low solidifying point.

A waxy ester of an unsaturated fatty acid mixture produced by a reduction reaction or distillation of the reduction product with unsaturated alcohol can also be used as the material to be reduced.

Reduction Reaction

Preferably the vegetable unsaturated fatty acid as the foregoing raw material and/or an alkyl ester thereof having 1 to 4 alkyl carbon atoms is reduced at high temperature and under high pressure by a fixed bed continuous reaction method using a zinc-type catalyst having a copper content of 30 ppm or less.

It is preferable that the copper content of the zinc-type catalyst be 20 ppm or less, especially 10 ppm or less. It is most preferable that the zinc-type catalyst contains substantially no copper. If the copper content is within the above ranges, the cloud point of the obtained unsaturated alcohol will not be overly high.

Examples of the zinc-type catalyst are not limited and include those known as catalysts for reduction of fatty acids, such as zinc-chrome oxide, zinc-aluminum oxide, zinc-aluminum-chrome oxide, zinc-chrome-manganese oxide, zinc-iron oxide and zinc-iron-aluminum oxide. Zinc-chrome oxide is especially preferable. Such zinc-type catalysts may be used singly or in combination.

Such catalysts may be used as is or may be used supported on carriers such as silica, alumina, diatomaceous earth, clay, carbon, and graphite to increase their strength.

Such carrier-supported-type catalysts can be used without limitation and can be prepared by impregnation methods, coprecipitation methods and like prior art methods. Powders or pastes produced in these ways may be made into molded catalysts in a suitable form by known machines, including tabletting devices, granulators, extrusion molding machines and the like.

When reduction is conducted by a fixed-bed continuous reaction, the molded catalyst is filled into a reaction tower. After activation, the reaction is preferably performed by allowing hydrogen and the vegetable unsaturated fatty acid mixture and/or alkyl ester thereof having 1 to 4 alkyl carbon atoms to flow in a downward or upward cocurrent stream.

It is preferable that the reaction temperature be in the range of about 250 to about 350° C., especially in the range of about 250 to about 300° C., further especially in the range about 270 to about 300° C. It is preferable that the reaction pressure be in the range of about 5 to about 35 MPa, especially in the range of about 15 to about 30 Mpa, further especially in the range of about 20 to about 30 MPa. The superficial velocity in the raw material supply tower is in the range of about 1/20 to about 1/1 h$^{-}$1.

A liquid vegetable unsaturated alcohol mixture having an iodine value of about 88 to about 100 and a cloud point of less than 7° C. can be thereby obtained.

When required, distillation of the crude reduction product can concentrate components having 18 carbon atoms and can remove impurities such as small amounts of dissolved zinc or other metal ions, fine catalyst particles and the like. It is preferable that the distillation is carried out at a temperature within the range of about 150 to about 250° C. and a pressure within the range of about 0.1 to about 15 KPa.

A waxy ester of an unsaturated fatty acid with the obtained unsaturated alcohol can be produced by distillation using a transesterification catalyst, such as NaOH, KOH, titanium tetrabutoxide or the like, in a content of about 5 to about 300 ppm. The ester can be re-used as the material to be used for the reduction reaction.

Slight Hydrogenation

Further, the obtained liquid vegetable unsaturated alcohol is preferably slightly hydrogenated. The term "slight hydrogenation" used herein refers to a procedure in which a conjugated diene moiety is substantially selectively hydrogenated to a monoene moiety, i.e., resulting in hydrogenation without increase of cloud point.

Useful catalysts for slight hydrogenation are copper-containing catalysts such as copper, copper-zinc, copper-chrome, copper-zinc-chrome and oxides thereof, and modified catalysts comprising a mixture of the above catalysts with molybdenum, tungsten, magnesium, barium, aluminum, calcium, zirconium, manganese and their oxides.

Specific examples are copper oxide, copper-zinc-chrome oxide, copper-chrome-zinc-magnesium oxide, copper-zinc-chrome-barium oxide, copper-zinc oxide, copper-zinc-magnesium oxide, copper-zinc-aluminum oxide, copper-chrome oxide, copper-chrome-magnesium oxide, copper-chrome-manganese oxide, copper-chrome-barium oxide, copper-chrome-barium-magnesium oxide, copper-chrome-manganese-barium oxide, copper-chrome-manganese-magnesium oxide, copper-calcium-silicic acid, etc. Especially preferred are copper-zinc oxide, copper-chrome-oxide, copper-chrome-manganese oxide, copper-chrome-barium oxide, copper-chrome-manganese-barium oxide, copper-zinc-aluminum oxide and copper-calcium-silicate, etc. Particularly preferable are copper-zinc oxide, copper-zinc-aluminum oxide and copper-calcium-silicate.

Catalysts for slight hydrogenation can be used singly or in combination.

Commercially available catalysts are usable as such catalysts, such as N-203, N203S, N203SD, N203SDB, E01-X1, and X213 (products of Nikki Co. Ltd.); Cu-0202P, Cu-1106P, Cu-1800P, Cu1850P, Cu-1950P, Cu-0891P (products of Engelhard Corp.); CB-2, C-5A, C-100, C-700, C-900, CUZ001 (products of Sakai Chemical Industry Co., Ltd.); etc.

Such catalysts for slight hydrogenation may be used as is, or may be used supported on carriers such as silica, alumina, diatomaceous earth, clay, carbon and graphite to increase the strength.

It is preferable that the amount of catalyst used be about 0.05 to 1 wt. %, especially about 0.1 to 0.5 about wt. %, and further especially about 0.1 to about 0.2 wt. %, based on the raw material unsaturated alcohol. When the amount of catalyst is too small, it is difficult to attain a satisfactory reaction rate for practical use. On the other hand, if the catalyst is used in an excessive amount, reaction selectivity is diminished, resulting in a tendency to decrease the content of conjugated diene and a likelihood of lowering the iodine value. If the catalyst is used in an amount within the above ranges, such problems do not occur.

The slight hydrogenation methods are not limited, and include, for example, batch suspension bed reaction method, continuous suspension bed reaction, fixed bed continuous reaction, etc.

When batchwise or continuous suspension bed reaction methods are used, it is preferable that the reaction temperature be in the range of about 100 to about 200° C., more preferably about 120 to about 170° C., and further especially about 140 to about 160° C. It is preferable that the reaction pressure be in the range of about 1 MPa to atmospheric pressure, especially about 0.5 to about 0.05 Mpa, and further especially about 0.1 to about 0.3 MPa. If slight hydrogenation temperature or pressure is too high, the cloud point is increased, whereas if it is too low, a satisfactory reaction rate can not be attained for practical use. If the temperature and pressure are within the above ranges, such problems do not occur.

When the slight hydrogenation reaction is carried out by a fixed bed continuous reaction method, the molded catalyst is filled into a reaction tower. After activation, the reaction is then preferably performed by allowing unsaturated alcohol and hydrogen to flow in a downward cocurrent stream or upward cocurrent stream. It is preferable that the reaction temperature is within the range of about 50 to about 150° C., especially in the range of about 50 to about 100° C., and further especially in the range of about 60 to about 80° C. It is preferable that the reaction pressure be within the range of about 1 MPa to atmospheric pressure, especially in the range of about 0.5 to about 0.05 MPa, and further especially in the range of about 0.3 to about 0.1 MPa. If the temperature or pressure of the slight hydrogenation reaction is too high, the cloud point is increased, whereas if it is too low, a satisfactory reaction rate for practical use is not attained. If the temperature and pressure are in the above ranges, such problems do not arise.

The materials for slight hydrogenation may be a crude reduction product or a distillate of a crude reduction product.

Such slight hydrogenation gives an unsaturated alcohol mixture having an iodine value of about 88 to about 100, a cloud point of less than 7° C., and a conjugated diene content of 1 wt. % or less.

Distillation

When the obtained unsaturated alcohol mixture is distilled, a concentrate of the component having 18 carbon atoms, especially a concentrate of oleyl alcohol, is produced.

When distillation is effected in the process of the invention, any of the following materials (1) to (3) may be the distill, and the materials (1) to (3) may be used duplicatively:
(1) a fatty acid mixture obtained by hydrolysis of vegetable oil and/or alkyl esters thereof;
(2) an unsaturated alcohol mixture obtained by reduction of a fatty acid mixture and/or alkyl esters thereof (crude reduction product); and
(3) an unsaturated alcohol mixture obtained by slight hydrogenation.

Deodorization

The process of the invention may include a deodorization step. Deodorization is performed on an unsaturated alcohol mixture obtained by reduction of a vegetable fatty acid mixture and/or alkyl esters thereof. The deodorization may be done after distillation, slight hydrogenation or the like. It is the most preferable to effect the deodorization immediately before the completion of the production process.

Deodorization methods include known methods for deodorization of unsaturated alcohols, including, for example, steam deodorization, vacuum topping, thin film distillation, activated carbon adsorption and the like, among which steam deodorization is preferred. Steam deodorization may be executed in combination with other deodorization methods.

Steam deodorization is preferably carried out by blowing steam into an unsaturated alcohol mixture at a temperature of about 100 to about 200° C. and a pressure of about 0.1 to about 70 KPa. It is preferable that the amount of steam blown is about 0.1 to about 20 wt. %, and especially about 0.5 to about 10 wt. %, calculated as the weight of water based on the unsaturated alcohol mixture.

It is especially preferable to carry out steam deodorization at a temperature of about 120 to about 150° C. and a pressure of about 0.1 to about 70 KPa. It is preferable that the amount of steam blown in this operation is about 1 to 20 wt. %, and especially about 1 to about 8 wt. %, calculated as the weight of water based on the unsaturated alcohol mixture.

It is particularly preferable that the temperature is about 120 to about 150° C., the pressure is about 0.1 to about 70 KPa, and the amount of steam blown is about 1 to about 10 wt. %, and especially about 1 to 8 wt. %, calculated as the weight of water based on the unsaturated alcohol mixture.

If the amount of steam blown is too small, the deodorization effect is insufficient, whereas if it is too large, the unsaturated alcohol mixture to be deodorized is distilled off, and the unsaturated alcohol mixture is obtained in a reduced yield. If the amount of steam is within the above ranges, such problems do not arise.

Preferred deodorization methods include a method in which an unsaturated alcohol mixture as a crude reduction product or an unsaturated alcohol mixture obtained by slight hydrogenation is distilled and the initial and end-run distillate fractions are cut. In this case, the amount of initial distillate fractions cut is about 3 to about 10 wt. % based on the amount of raw materials used, and the amount of the end-run distillate fractions cut is about 10 to about 25 wt. % based on the amount of raw materials used. Accordingly the distillation and deodorization can be done at the same time.

Depending on the entire procedure plan and the structure of the product to be manufactured, it is decided which is selected: a steam deodorization method excellent in the yield, or a distillation method having fewer steps but in which the initial and the end-run distillate fractions are cut.

A deodorization step removes odorous components, giving a scarcely odorous unsaturated alcohol mixture. The odorous components include various components that are relatively volatile, such as short-chain saturated or unsaturated aldehydes.

The completion of the deodorization step can be confirmed by organoleptic evaluation and can be objectively confirmed by values acquired by head-space gas chromatography or a smell sensor.

By such a deodorization step, a substantially odorless unsaturated alcohol is obtained. If the obtained unsaturated alcohol mixture is heated at 150° C. for 10 minutes, the amount of volatile components of the alcohol is 500 ppm or less based on the unsaturated alcohol mixture as measured by head space gas chromatography.

(2) Unsaturated Alcohol Mixture of the Invention

The unsaturated alcohol mixture of the invention is liquid vegetable unsaturated alcohol mixture having an iodine value of about 88 to about 100 and a cloud point of less than 7° C.

Cloud points referred to in this invention are determined according to the method under JIS K 2269.

If the unsaturated alcohol mixture has too high an iodine value, too great a content of linoleic alcohol exists in the unsaturated alcohol mixture, and it is difficult to maintain a good color stability. If the unsaturated alcohol mixture has too low an iodine value, too high a saturated alcohol content is present, and it is difficult to keep a liquid state at environmental temperatures for use and for preservation. If the values are within the above ranges, such problems do not arise.

If the cloud point is too high, small amounts of components are likely to become crystallize and cloudiness or turbidity tends to occur during storage. For example, a liquid product becomes partly crystalline within a drum or the like and crystals are precipitated to partially alter the formulation of the product which is a serious defect in a liquid product. If the contents are within the specified ranges, such problems should not arise.

The cloud point is preferably 6° C. or lower. The minimum cloud point value is not limited, but is usually about 4° C.

It is preferable that the unsaturated alcohol mixture of the invention has a conjugated diene content of 1 wt. % or less, especially 0.5 wt. % or less, and further especially 0.2 wt. % or less. If the conjugated diene content is too great, the product may become colored during conversion of the unsaturated alcohol into derivatives because of the low color stability in the presence of acids or bases, or may become colored during storage because of poor long-term color stability against light. If the contents are within the above ranges, the unsaturated alcohol mixture is superior in color stability in the presence of acids or bases and long-term color stability against light.

Cosmetics are required to have a storage stability of 3 years. When cosmetics are stored for such a long time, they are not necessarily disposed in a cool and dark place so that materials for cosmetics need to retain a light stability for about 3 years. If the conjugated diene content is usually 1 wt. % or less, especially 0.5 wt. % or less, and further especially 0.2 wt. % or less, such long-term light stability can be achieved.

It is preferable that when the unsaturated alcohol mixture of the invention is heated at 150° C. for 10 minutes, the content of volatile components is usually 500 ppm or less, especially 100 ppm or less, and further especially 50 ppm or less, as measured by head space gas chromatography. If the volatile component content is too high, the odor of the components is emitted from the unsaturated alcohol mixture itself, and the smell of the product comprising the unsaturated alcohol or its derivative may change or a longer time may be involved in emission of the smell. If the contents are within the specified range, such problems do not arise.

It is preferable that the unsaturated alcohol mixture of the invention contains 70 wt. % or more, especially at least 85 wt. %, of oleyl alcohol. The maximum amount of oleyl alcohol content is not limited. Even 100 wt % content may be allowable. If the oleyl alcohol content is too low, the alcohol mixture may have reduced stability to oxidation. But if the content of oleyl alcohol is within the above ranges, such a problem should not arise.

Derivatives

The unsaturated alcohol mixture of the invention can be made into the following derivatives.

(a) A lower alkylene oxide adduct of the unsaturated alcohol mixture of the invention. Lower alkylene oxides include, for example, alkylene oxides having 2 or 3 carbon atoms. Examples of such alkylene oxide are ethylene oxide, trimethylene oxide and 1-methyl ethylene oxide. The average addition number of the alkylene oxide is usually 1 to 100, and preferably 2 to 50.

(b) A sodium salt, a potassium salt, a triethanolamine salt or an ammonium salt of a sulfuric acid ester of the unsaturated alcohol mixture of the invention or an (a) alkylene oxide adduct thereof. The sulfuric acid ester may be either di-substituted ester or mono-substituted ester (half or hemi ester).

(c) A carboxylic acid ether of the unsaturated alcohol mixture of the invention or an (a) alkylene oxide adduct thereof, or a sodium salt, a potassium salt, a triethanolamine salt or an ammonium salt of the ether carboxylic acid.

Carboxylic acid ethers of the invention or sodium, potassium, triethanolamine and ammonium salts of such carboxylic acid ethers include compounds prepared by converting the alcohol as the raw material or an (a) alkylene oxide adduct thereof into an alcoholate with alkali and adding monochloroacetic acid to form an ether linkage. The carboxylic acid ether of the invention is represented by formula (1)

$$R^1O\text{—}(R^2O)_n\text{—}CH_2COOX \quad (1)$$

wherein $R^1$ is the residue of the unsaturated alcohol mixture of the invention, $R^2$ is an ethylene group, a propylene group, or 1-methyl ethylene group, X is H, Na, K, triethanolamine or ammonium, and n is an integer of 0 to 100 on an average.

(d) Mono-, di- or tri-phosphoric ester of the unsaturated alcohol mixture of the invention or an (a) alkylene oxide adduct thereof or sodium, potassium, atriethanolamine or ammonium salts of the phosphoric acid ester.

(e) An ester of the unsaturated alcohol mixture of the invention with a saturated or unsaturated fatty acid having 12 to 22 carbon atoms.

(f) A lactic acid ester of the unsaturated alcohol mixture of the invention.

Use

The unsaturated alcohol of the invention can be suitably used as a material for detergent compositions for clothing, kitchen tools or instruments and household articles, and as a material for textile oils and the like.

In these cases, the unsaturated alcohol of the invention can be used as it is, or as a derivative. Examples of such derivatives are alkylene oxide adducts, salts of sulfate esters, salts of sulfate esters of alkylene oxide adducts, esters with fatty acids, ethers of carboxylic acids, phosphate esters and the like.

The unsaturated alcohol of the invention can be suitably used in products for personal care, e.g., as a material for cosmetics for hair care such as shampoos, hair rinses, hair treatments and the like; and cosmetics for body care such as skin creams, skin lotions, hand soaps, body soaps and the like. The unsaturated alcohol of the invention is especially suitable for base materials for personal care products.

In these cases, the unsaturated alcohol of the invention can be used as it is, or as a derivative. Examples of such derivatives are fatty acid esters, lactic acid esters, alkylene oxide adducts, salts of sulfate esters, salts of sulfate esters of alkylene oxide adducts, phosphoric acid esters (especially triesters), phosphoric acid esters of alkylene oxide adducts (especially partial esters) and salts thereof, ethers of carboxylic acids and salts thereof and the like.

When the unsaturated alcohol of the invention is used as a material for cosmetics, it is desirable to use an unsaturated alcohol mixture which has been subjected to a distillation step and/or a deodorization step so as to contain the smallest possible amount of odorous components.

EXAMPLES

The invention will be described below with reference to the following examples and test examples to which, however, the invention is not limited.

In the following examples, the cloud point was measured according to JIS K 2269. The color (Hazen) was measured according to JIS K 0071-1. The color (Gardner) was measured according to JIS K 0071-2. In a glc composition, a fatty acid composition "Fn" such as "F1", "F2" or the like means that the unsaturated fatty acid has "n" double bond(s).

Example 1

The fatty acid mixture obtained by hydrolysis of palm kernel oil was distilled and the solid was fractionated by cooling, giving an unsaturated fatty acid mixture (iodine value 93.4, glc composition C12: 0.6%, C14: 0.6%, C16: 5.5%, C18: 1.4%, C18F1: 79.3%, C18F2: 11.8%, C18F3: 0.5%, C20F1: 0.3%) (product of Acidchem Inc., trade name "PALMAC 750"). A methyl ester thereof was prepared by esterification of 10 kg of PALMAC 750 with 10 kg of methyl alcohol and 0.1 kg of p-toluenesulfonic acid. The obtained methyl ester was used as a raw material and reduced in the presence of a zinc-chrome oxide catalyst containing 5 ppm of copper at a reaction pressure of 20 MPa, a reaction temperature of 290° C., and a superficial velocity of $0.3/h^{-1}$ (in the tower for supply of raw materials). The obtained crude reduction product was distilled, whereby the following unsaturated alcohol mixture was produced:

| Iodine value | 89.7 |
|---|---|
| Cloud point | 4.1° C. |
| Composition | |
| C12 | 0.2% |
| C14 | 0.6% |
| C16 | 5.9% |
| C18 | 1.8% |
| C18F1 | 81.9% |
| C18F2 | 2.9% |
| C20F1 | 0.3% |
| Conjugated diene | 6.4% |

Comparative Example 1

The same procedure as in Example 1 was conducted except that a zinc-chrome oxide catalyst containing 78 ppm of copper was used. The obtained unsaturated alcohol mixture had a cloud point of 10° C.

Example 2

A fatty acid mixture obtained by hydrolysis of palm kernel oil was distilled and the solid was fractionated by cooling, giving unsaturated fatty acid (iodine value 93.4, glc composition C12: 0.6%, C14: 0.6%, C16: 5.5%, C18: 1.4%, C18F1: 79.3%, C18F2: 11.8%, C18F3: 0.5%, C20F1:0.3%) (product of Acidchem Inc., trade name "PALMAC 750"). A methyl ester thereof was prepared by esterification of 10 kg of PALMAC 750 with 10 kg of methyl alcohol and 0.1 kg of p-toluenesulfonic acid. The obtained methyl ester was used as a raw material and reduced in the presence of a zinc-chrome oxide catalyst containing 5 ppm of copper at a reaction pressure 20 MPa, a reaction temperature of 290° C., and a superficial velocity of 0.3/h$^{-1}$ (in the tower for supply of raw materials), whereby a crude reduction product was obtained.

A 5-liter volume electromagnetic agitation type autoclave was provided with 1500 g of the obtained crude reduction product, and 2.3 g of a copper-zinc-aluminum oxide catalyst (product of Nikki Co., Ltd., trade name "E01-X1"). The air inside of the system was replaced with hydrogen and a reaction was carried out at 150 to 160° C., and a hydrogen pressure of 0.1 to 0.2 MPa for three hours. After cooling, the catalyst was filtered off. The residue (1000 g) was placed in a Claisen flask with a Widmer-type fractionator (45 cm) fixed thereto, and vacuum distillation was performed. After distilling off the initial distillate fractions in an amount of 6 wt. % based on the amount of materials used, distillation was continued until the yield of the main distillate amounted to 80 wt. %, whereby the following unsaturated alcohol mixture was produced:

| | |
|---|---|
| Iodine value | 90.9 |
| Cloud point | 4.1° C. |
| Composition | |
| C16 | 4.8% |
| C18 | 1.9% |
| C18F1 | 89.9% |
| C18F2 | 2.5% |
| C20F1 | 0.1% |
| Conjugated diene | 0.1% |
| Color (Hazen) | 10 |

Example 3

A fatty acid mixture obtained by hydrolysis of palm oil was distilled and the solid was fractionated by cooling, giving unsaturated fatty acid (iodine value 98.3, glc composition C14: 0.5%, C16: 5.0%, C18: 1.8%, C18F1: 74.5%, C18F2: 18.1%, C20F1: 0.1%). A methyl ester thereof was prepared by esterification of 10 kg of the obtained fatty acid with 10 kg of methyl alcohol and 0.1 kg of p-toluenesulfonic acid. The obtained methyl ester was used as a raw material and reduced in the presence of a zinc-chrome oxide catalyst containing 15 ppm of copper at a reaction pressure of 20 MPa, a reaction temperature of 290° C., and a superficial velocity of 0.3/h$^{-1}$ (in the tower for supply of raw materials). The following unsaturated alcohol mixture was produced by distillation of the crude reduction product:

| | |
|---|---|
| Iodine value | 96.8 |
| Cloud point | 3.4° C. |
| Composition | |
| C14 | 0.4% |
| C16 | 5.3% |
| C18 | 2.0% |
| C18F1 | 77.7% |
| C18F2 | 5.3% |
| C20F1 | 0.1% |
| Conjugated diene | 9.2% |

Example 4

Slight Hydrogenation/Deodorization

A 5-liter volume electromagnetic agitation type autoclave was provided with 1500 g of the unsaturated alcohol mixture obtained in Example 1 and 2.3 g of a copper-chrome-manganese-barium oxide catalyst (product of Sakai Chemical Co., Ltd., trade name "C-900"). The air inside of the system was replaced with hydrogen and a reaction was carried out at 150 to 160° C., and a hydrogen pressure of 0.1 to 0.2 MPa for three hours. After cooling, the catalyst was filtered off.

The residue (1000 g) was placed in a Claisen flask with a Widmer-type fractionator (45 cm) fixed thereto. Vacuum distillation was performed. After distilling off the initial distillate fractions in an amount of 6 wt. % based on the amount of materials used, the main distillate fraction was distilled off. The yield of the main distillate was 91 wt. %. The main distillate was then subjected to steam distillation at 140° C. and 1.1 KPa, whereby the following unsaturated alcohol mixture was produced. The amount of steam blown in this operation was 2 wt. % based on water:

| | |
|---|---|
| Iodine value | 91.6 |
| Cloud point | 3.8° C. |
| Composition | |
| C16 | 4.4% |
| C18 | 1.8% |
| C18F1 | 90.6% |
| C18F2 | 2.9% |
| C20F1 | 0.2% |
| Conjugated diene | 0.1% |
| Color (Hazen) | 10 |

Example 5

Slight Hydrogenation/Deodorization

The same procedure as in Example 4 was conducted except that the unsaturated alcohol mixture obtained in Example 3 was used and a copper-zinc-aluminum oxide catalyst (product of Nikki Co., Ltd., trade name "E01-X1") was used as a copper-containing catalyst for slight hydrogenation. The procedure gave the following unsaturated alcohol mixture.

| | |
|---|---|
| Iodine value | 96.1 |
| Cloud point | 4.4° C. |
| Composition | |
| C16 | 4.5% |
| C18 | 2.2% |

-continued

| | |
|---|---|
| C18F1 | 87.8% |
| C18F2 | 5.2% |
| C20F1 | 0.1% |
| Conjugated diene | 0.2% |
| Color (Hazen) | 10 |

Example 6

Slight Hydrogenation

A 5-liter volume electromagnetic agitation type autoclave was provided with 1500 g of the unsaturated alcohol mixture obtained in Example 1 and 2.3 g of a copper-chrome oxide catalyst. The air inside of the system was replaced with hydrogen and a reaction was carried out at 150 to 160° C., and a hydrogen pressure of 0.1 to 0.2 MPa for three hours. After cooling, the catalyst was filtered off. The residue (1000 g) was placed in a Claisen flask with a Widmer-type fractionator (45 cm) fixed thereto. Vacuum distillation was performed. After distilling off the initial distillate fractions in an amount of 6 wt. % based on the amount of materials used, the main distillate fraction was distilled off. The yield of the main distillate was 91 wt. %. The above-mentioned procedure gave the following unsaturated alcohol mixture:

| | |
|---|---|
| Iodine value | 91.0 |
| Cloud point | 3.5° C. |
| Composition | |
| C12 | 0.2% |
| C14 | 0.6% |
| C16 | 5.9% |
| C18 | 1.8% |
| C18F1 | 88.9% |
| C18F2 | 2.9% |
| C20F1 | 0.1% |
| Conjugated diene | 0.1% |
| Color (Hazen) | 15 |

Example 7

Example of Production of Hair Conditioner

Dissolved in deionized water with stirring were 2 wt. % of the unsaturated alcohol mixture of Example 4, 1 wt. % of meadowfoam seed oil, 2.5 wt. % of stearic acid amide propyl dimethylamine lactate, 0.5 wt. % of hydrolyzed keratin, and 1 wt. % of hydrolyzed wheat protein. The solution was adjusted to a pH of 4.0 with lactic acid, and then heated with stirring for 1 hour at 85° C. for sterilization. After cooling, a herb-type perfume was added to produce hair conditioner.

Examples 8 to 11

Examples of Production of Alkylene Oxide Adducts

Potassium hydroxide (0.1 wt. %) was added to samples of each of the unsaturated alcohol mixtures prepared in Examples 1, 2, 4 and 6, and ethylene oxide was then added thereto at 170° C. The obtained product was transparent and clear.

Table 1 shows the number of moles of ethylene oxide added per mole of unsaturated alcohol prepared in Examples 8 to 11 and the corresponding color (Hazen).

TABLE 1

| Moles of ethylene oxide added per mole of unsaturated alcohol | Color (Hazen) Example | | | |
|---|---|---|---|---|
| | Example 8 | Example 9 | Example 10 | Example 11 |
| | Unsaturated alcohol (raw material) | | | |
| | Example 1 | Example 2 | Example 4 | Example 6 |
| 2 | 45 | 25 | 25 | 35 |
| 3 | 40 | 25 | 25 | 30 |
| 4 | 35 | 20 | 20 | 25 |
| 5 | 35 | 20 | 20 | 25 |
| 6 | 35 | 20 | 20 | 25 |
| 7 | 35 | 20 | 20 | 25 |
| 8 | 35 | 20 | 20 | 25 |
| 9 | 35 | 20 | 20 | 25 |
| 10 | 35 | 20 | 20 | 25 |
| 12 | 35 | 20 | 20 | 25 |
| 15 | 35 | 20 | 20 | 25 |
| 16 | 35 | 20 | 20 | 25 |
| 20 | 40 | 20 | 20 | 25 |
| 23 | 40 | 20 | 20 | 25 |
| 25 | 40 | 20 | 20 | 25 |
| 30 | 45 | 25 | 25 | 30 |
| 40 | 45 | 25 | 25 | 30 |
| 44 | 45 | 30 | 30 | 35 |
| 50 | 50 | 30 | 30 | 35 |

As is apparent from Table 1, all the ethylene oxide adducts show a color (Hazen) sufficiently low for practical use.

Example 12

Example of Production of Alkylene Oxide Adduct

Potassium hydroxide (0.2 wt. %) was added to the unsaturated alcohol mixture of Example 1. Then, 3 mol of propylene oxide was reacted for addition at 170° C., and then 5 mol of ethylene oxide was reacted for addition. The obtained product was transparent and clear and was found to have a color (Hazen) as good as 50.

Example 13

Example of Production of Sulfate Ester 117 g (equimolar: 1 mol/1 mol) of chlorosulfonic acid was added to 267 g of the unsaturated alcohol mixture of example 1 to give an acidic hemiester. An aqueous solution of sodium hydroxide was added for neutralization. The obtained product was transparent and clear and was found to have a color (Hazen) as good as 50.

Another product obtained by the addition of an aqueous solution of potassium hydroxide for neutralization was transparent and clear and also found to have a color (Hazen) as good as 50.

Example 14

Example of Production of Purely Vegetable Oleyl Oleate 1000 g of PALMAC 750 used as the unsaturated fatty acid mixture in Example 1, 940 g of unsaturated alcohol mixture of Example 4 as the unsaturated alcohol, and 0.5 wt. % of p-toluenesulfonic acid were used. Esterification by dehydration was carried out at 110° C. for 4 hours at a pressure within the range of from atmospheric pressure to 0.1 KPa. The ester was then neutralized, washed with water and dried, giving a purely vegetable unsaturated ester mixture. The obtained ester mixture was odorless, transparent and clear and was found to have a color (Hazen) as good as 30.

Example 15

Example of Production of Lactic Acid Ester 135 g of the unsaturated alcohol mixture of Example 4, 47 g of lactic acid and 0.5 wt. % of p-toluenesulfonic acid were used. Esterification by dehydration was carried out at 110° C. for 5 hours at a pressure within the range of from atmospheric pressure to reduced pressure(0.1 KPa). The lactic acid ester obtained was neutralized, washed with water and dried, giving an odorless, transparent and clear product which was found to have a color (Hazen) as good as 50.

Examples 16 to 19

Example of Production of Carboxylic Acid Ethers

Sodium hydroxide (4.4 g) was added to 49 g of each of the 5-mole ethylene oxide adducts of unsaturated alcohols prepared in Examples 8 to 11. Each mixture was then dehydrated at 120° C. under reduced pressure and 13 g of sodium monochloroacetate was added. The mixture was maintained at 120° C. under reduced pressure for 3 hours and was then made acidic by the addition of diluted hydrochloric acid. The mixture was then heated to 90° C. and left to stand. The lower aqueous layer then was removed to give carboxylic acid ethers of ethylene oxide adducts of unsaturated alcohols.

The carboxylic acid ether was neutralized with sodium hydroxide to produce 23 wt. % aqueous solutions.

Table 2 shows the number of moles of added ethylene oxide to each carboxylic acid ether and the sodium salts thereof and the corresponding color (Hazen).

TABLE 2

| Moles of ethylene oxide added per mole of unsaturated alcohol | Color (Hazen) | | | |
|---|---|---|---|---|
| | Example 16 | Example 17 | Example 18 | Example 19 |
| | Unsaturated alcohol (as raw material) | | | |
| | Example 1 | Example 2 | Example 4 | Example 6 |
| Carboxylic acid ether | | | | |
| 2 | 150 | 80 | 80 | 90 |
| 5 | 150 | 80 | 80 | 100 |
| 9 | 170 | 90 | 90 | 100 |
| Sodium salt | | | | |
| 2 | 50 | 25 | 25 | 30 |
| 5 | 50 | 30 | 30 | 35 |
| 9 | 55 | 30 | 30 | 40 |

As apparent from Table 2, each ethylene oxide adduct is sufficiently low in color (Hazen) for practical use.

Examples 20 to 23

Example of Production of Phosphoric Ester Ethers 7 g of phosphorus pentoxide was mixed with each of the ethylene oxide 5-mole adducts (49 g) of unsaturated alcohol mixtures prepared in Examples 1, 2, 4 and 6, and stirred at 50° C. for 3 hours, giving phosphoric ester ethers of ethylene oxide adducts of unsaturated alcohol mixtures.

Table 3 shows the ethylene oxide addition number of the obtained phosphoric ester ethers and the corresponding color (Hazen).

TABLE 3

| Moles of ethylene oxide added per mole of unsaturated alcohol | Color (Hazen) | | | |
|---|---|---|---|---|
| | Example 20 | Example 21 | Example 22 | Example 23 |
| | Unsaturated alcohol (raw material) | | | |
| | Example 1 | Example 2 | Example 4 | Example 6 |
| 2 | 100 | 70 | 70 | 80 |
| 3 | 100 | 70 | 70 | 80 |
| 4 | 100 | 70 | 70 | 90 |
| 5 | 100 | 70 | 70 | 90 |
| 10 | 100 | 80 | 80 | 90 |
| 20 | 100 | 80 | 80 | 90 |

As apparent from Table 3, each ethylene oxide adduct showed a color (Hazen) sufficiently low for practice.

Example 24

Example of Production of Hair Rinse From Oleyl Alcohol Ethylene Oxide Adduct

Dissolved in deionized water with stirring at 80° C. were 0.2 wt. % of the purely vegetable oleyl alcohol ethylene oxide 7-mole adduct prepared in Example 10 and 2.0 wt. % of cetyl trimethyl ammonium chloride. Slowly added thereto with stirring at the same temperature were 1.8 wt. % of Conol 30RC (product of New Japan Chemical Co., Ltd.: prepared from palm kernel oil), 0.2 wt. % of PALMAC 90-18 (product of Acidchem Inc., prepared from palm oil) and 2.2 wt. % of liquid paraffin. The mixture was cooled to 40° C. or below, whereby hair rinse was produced.

The obtained hair rinse was in the form of a white emulsion, had a pH of 3, and a good color in such an acidic state.

Example 25

Example of Production of Hair Rinse From Oleyl Alcohol Ethylene Oxide Adduct and Oleyl Oleate Ester Dissolved in deionized water with stirring at 80° C. were 0.2 wt. % of the purely vegetable oleyl alcohol ethylene oxide 7-mole adduct prepared in Example 9 and 2.0 wt. % of cetyl trimethyl ammonium chloride. Slowly added thereto with stirring at the same temperature were 1.8 wt. % of Conol 30RC (product of New Japan Chemical Co., Ltd.: prepared from palm kernel oil), 0.2 wt. % of PALMAC 90-18 (product of Acidchem Inc., prepared from palm oil) and 2.2 wt. % of the purely vegetable oleyl oleate prepared in Example 14. After cooling to 40° C. or below, a herb-type perfume was added, whereby hair rinse was produced.

The obtained hair rinse was in the form of white emulsion, had a pH of 3 and a good color in such an acidic state. The product scarcely emitted odor and showed no change in the smell of perfume. The time taken in emission of perfume was constant.

Example 26

Example of Production of Hair Rinse From Lactic Acid Ester and Ethylene Oxide Adduct Dissolved in deionized water were 0.2 wt. % of the purely vegetable oleyl alcohol ethylene oxide 7 mole adduct of Example 9 and 2.0 wt. % of cetyl trimethyl ammonium chloride at 80° C. Slowly added thereto with stirring at the same temperature were 1.8 wt. % of Conol 30RC (product of New Japan Chemical Co., Ltd.: prepared from palm kernel oil), 0.2 wt. % of PALMAC 90-18 (product of Acidchem Inc., prepared from palm oil) and 2.2 wt. % of the oleyl lactate of Example 15. After cooling to 40° C. or below, a herb-type perfume was added, whereby hair rinse was produced.

The obtained hair rinse and was in the form of white emulsion, had a pH of 3, and a good color in such an acidic state. The product scarcely emitted any odor and showed no change in the smell of the perfume. The time taken in emission of perfume was constant.

Example 27

Production of Body Soap From Ether Carboxylic Acid

Dissolved in deionized water with stirring were 5.5 wt. % of palm kernel oil-derived lauric acid, 5.2 wt. % of palm kernel oil-derived myristic acid, 2.0 wt. % of palm oil-derived palmitic acid, 0.2 wt. % of a chelating agent (CHELEST HS, product of CHELEST Co., Ltd.) and 6.9 wt. % of potassium hydroxide at 80° C. for 2 hours. The solution was then neutralized. Added thereto were 10 wt. % of an aqueous solution of lauryl dimethyl aminoacetic acid betaine (30 wt. %) and 6.2 wt. % of the sodium carboxylate ether of the ethylene oxide 5-mole adduct prepared in Example 16. The solution was cooled to 40° C. or below, whereby body soap was produced.

The obtained body soap had a pH of 10. The body soap produced by heating in such a basic state had a color(Hazen) as good as 30.

Example 28

Example of Production of Shampoo From Phosphoric Ester

Dissolved in deionized water with stirring were 4 wt. % of the sodium phosphate ether of the ethylene oxide 5-mole adduct prepared in Example 23, 24 wt. % of an aqueous solution of lauric acid amide propyl betaine(30 wt. %), 4 wt. % of polyoxyethylene (EO 3 moles) di-sodium salt of sulfosuccinic acid lauryl ester, 10 wt. % of a sodium sulfate of polyoxyethylene (EO 5 moles) coconut fatty acid monoethanolamide, 3 wt. % of coconut fatty acid diethanolamide and 0.6 wt. % of cationic cellulose at 80° C. for 2 hours. A shampoo product was produced by cooling the solution to 40° C. or lower.

The obtained product had a pH of 7. The product produced by heating had a color (Hazen) of as good as 20.

<Low Temperature Behavior>

Placed separately into glass containers 4 cm in diameter and 10 cm in height with a lid were a liquid vegetable unsaturated alcohol mixture having a cloud point of 4.1° C. (unsaturated alcohol prepared in Example 1), a vegetable unsaturated alcohol mixture having a cloud point of 10° C. (unsaturated alcohol prepared in Comparative Example 1) and a liquid vegetable unsaturated alcohol mixture having a cloud point of 6.5° C. Each container was left to stand in an incubator set at 10° C. to observe the low-temperature behavior of each unsaturated alcohol mixture. The results are shown in Table 4.

TABLE 4

| Cloud point (° C.) | 1 day later | 2 weeks later | 1 month later |
|---|---|---|---|
| 4.1 | Clear | Clear | Clear |
| 6.5 | Clear | Clear | Precipitate on the bottom |
| 10 | Precipitate on the bottom | Large amount of precipitate | Large amount of precipitate |

As apparent from Table 4, the unsaturated alcohol mixture having a cloud point of 6.5° C. (lower than 7° C.) had good retention of liquidity, and the unsaturated alcohol mixture having a cloud point of 4.1° C. (lower than 6° C.) was significantly superior in retention of liquidity. On the other hand, the unsaturated alcohol mixture having a cloud point of 10° C. was observed to precipitate to the bottom 1 day after standing and had very poor retention of liquidity.

<Color Stability Test in the Presence of an Acidic Substance>

To each of unsaturated alcohol mixtures prepared in Examples 1, 2, 4, 5 and 6 was added 0.1 wt. % of p-toluenesulfonic acid as an acidic substance. Each mixture was then heated for 1 hour at 150° C. and observed for color (Gardner).

<Color Stability Test in the Presence of a Basic Substance>

To each of unsaturated alcohol specimens prepared in Examples 1, 2, 4, 5 and 6 was added 0.2 wt. % of potassium hydroxide as a basic substance. The potassium hydroxide was then dissolved in each alcohol under nitrogen stream, and the solutions were observed for color (Hazen).

The results of the color stability tests are shown in Table 5.

TABLE 5

| | Color in the presence of an acidic substance (Gardner) | Color in the presence of a basic substance (Hazen) |
|---|---|---|
| Example 1 | 5.5 | 180 |
| Example 2 | 3.0 | 30 |
| Example 4 | 2.5 | 25 |
| Example 5 | 3.0 | 30 |
| Example 6 | 4.0 | 60 |

As apparent from Table 5, in Example 2 further entailing slight hydrogenation and distillation over Example 1 involving only reduction of the unsaturated fatty acid mixture and distillation, and in Examples 4 and 5 further entailing slight hydrogenation, distillation and steam deodorization over Example 1, the obtained unsaturated alcohol mixture was significantly less colored than in Example 1. Further, in Example 6 entailing slight hydrogenation of the unsaturated alcohol mixture obtained in Example 1, the unsaturated alcohol mixture was more colored than in Examples 4 and 5 but was markedly less colored than in Example 1. It is clear from the above that the degree of coloring in the presence of an acidic substance or a basic substance is markably decreased by slight hydrogenation.

The hair conditioner (Example 7) containing the unsaturated alcohol mixture of Example 4 was prepared by heating at 85° C. for 1 hour in the presence of a lactic acid as the acidic substance (pH 4.0). No coloring was observed following visual inspection.

<Odor Test>

Two kinds of odor tests were carried out for the unsaturated alcohol mixtures prepared in Examples 1, 2, 4, 5 and 6 by allowing ten monitors to smell the mixtures in lidless containers and allowing ten monitors to smell the odor immediately after opening the lids of lided containers.

<Amount of Volatile Components>

The amount of volatile components in the unsaturated alcohol mixtures prepared in Examples 1, 2, 4, 5 and 6 was measured, when heated at 150° C. for 10 minutes, by head space gas chromatography. A sample in which a known amount of toluene was dissolved in liquid paraffin was used as a control sample. The amount of volatile components was expressed as a value calculated as toluene.

The results of the odor tests and measurements of the amounts of volatile components are shown in Table 6.

TABLE 6

|  | Odor Test | | Amount of volatile components (ppm) |
| --- | --- | --- | --- |
|  | Lidless container | On opening the container |  |
| Example 1 | Oily odor | Oily odor | 2000 |
| Example 2 | Odorless | Odorless | 50 |
| Example 4 | Odorless | Odorless | 50 |
| Example 5 | Odorless | Odorless | 50 |
| Example 6 | Odorless | Odorless | 120 |

As apparent from Table 6, in Example 1 entailing only reduction of the unsaturated fatty acid mixture and distillation, an oily odor was perceived from both the lidless container and the lid-opened container. On the other hand, in Example 2, further entailing slight hydrogenation and distillation over Example 1, in Examples 4 and 5 further entailing slight hydrogenation, distillation and steam deodorization over Example 1, and in Example 6 further entailing slight hydrogenation over Example 1, no odor was perceived from the lidless container or on opening the lid from the container, and the amount of volatile components was much smaller in Examples 2, 4 and 5 than in Example 1.

The hair conditioner (Example 7) containing the unsaturated alcohol prepared in Example 4 (Example 7) exhibited neither a change in the perfume smell nor a change in the time taken to emit the smell. This makes it clear that when a cosmetic product contains an unsaturated alcohol having 50 ppm of volatile components, the product involves neither a change in perfume smell nor a change in the time taken in emission of the smell.

<Stability of Coloring and Odor With Time>

The unsaturated alcohol mixture prepared in Example 1 (containing 6.4 wt. % of conjugated diene compound) and the unsaturated alcohol mixtures prepared in Examples 2 and 4 (containing 0.1 wt. % of conjugated diene compound) were placed in 4 cm-diameter, 10 cm-height containers with a lid, and were stored in an oven at 40° C. for 2 months. The specimens were observed to check their color (Hazen) and odor by the aforesaid methods.

The results were that the unsaturated alcohol specimens prepared in Examples 1, 2 and 4 had a color (Hazen) of less than 10 immediately after production, and had a color (Hazen) of 40 (Example 1) or 10 (Examples 2 and 4) after a 2-month storage.

In testing of the unsaturated alcohol of Example 1, 8 monitors out of 10 monitors perceived the odor immediately after production, and all 10 monitors perceived the odor 2 months later. In contrast, in testing the unsaturated alcohol mixtures of Examples 2 and 4, none of the 10 monitors perceived the odor either immediately after production and after a 2-month storage.

The above results show that the coloration and emission of odor resulting from long term storage at a relatively high temperature can be intensively suppressed by executing slight hydrogenation, distillation and steam deodorization.

<Long-Term Light Resistance>

The unsaturated alcohol mixture prepared in Example 1 (containing 6.4 wt. % of conjugated diene compound), the unsaturated alcohol mixture prepared in Example 2 (containing 0.1 wt. % of conjugated diene compound) and the unsaturated alcohol mixture prepared in Example 4 (containing 0.1 wt. % of conjugated diene compound) were separately placed in a 4 cm-diameter, 10 cm-height glass containers with a lid, exposed to sunlight outdoors for 2 months and were observed for coloring.

As the result, the unsaturated alcohol specimens prepared in Examples 1, 2 and 4 had a color (Hazen) of less than 10 immediately after production. After 2-months exposure to sunlight, the unsaturated alcohol of Example 1 had a color (Hazen) of 50 while the unsaturated alcohol specimens in Examples 2 and 4 showed a color (hazen) of 10. These results indicate that the long term light resistance can be significantly enhanced by executing slight hydrogenation, distillation and/or steam deodorization.

Example 29

Example of Lowering a Conjugated Diene Content to About 3 wt. % by Reduction

The fatty acid obtained by hydrolysis of palm kernel oil was distilled and the solid was fractionated by cooling, giving an unsaturated fatty acid (iodine value 93.4, glc composition C12: 0.6%, C14: 0.6%, C16: 5.5%, C18: 1.4%, C18F1: 79.3%, C18F2: 11.8%, C18F3: 0.5%, C20F1: 0.3%) (product of Acidchem Inc., trade name "PALMAC 750"). A methyl ester thereof was prepared by esterification of 10 kg of PALMAC 750 with 10 kg of methyl alcohol and 0.1 kg of p-toluenesulfonic acid. The obtained methyl ester was used as a raw material and reduced in the presence of a zinc-chrome oxide catalyst containing 5 ppm of copper at a reaction pressure of 20 MPa, a reaction temperature of 320° C., and a superficial velocity of $0.3/h^{-1}$ (in the tower for supply of raw materials). The obtained crude reduction product was distilled, whereby the following unsaturated alcohol mixture was produced:

| Iodine value | 87.3 |
| --- | --- |
| Cloud point | 6.9° C. |
| Composition | |
| C12 | 0.2% |
| C14 | 0.7% |
| C16 | 6.3% |
| C18 | 3.1% |
| C18F1 | 82.9% |
| C18F2 | 3.1% |
| C20F1 | 0.4% |
| Conjugated diene | 3.0% |

Example 30

Example of Lowering a Conjugated Diene Content to About 3 wt. % by Slight Hydrogenation A 5-liter vol. electromagnetic agitation type autoclave was provided with 1500 g of the unsaturated alcohol mixture prepared in Example 1, and 2.3 g of a copper-chrome-manganese-barium oxide catalyst (product of Sakai Chemical Co., Ltd., trade name "C-900"). The air inside the system was replaced with hydrogen and a reaction was carried out at 150 to 160° C. and a hydrogen pressure of 0.1 to 0.2 MPa for 30 minutes. After cooling, the catalyst was filtered off.

The residue (1000 g) was placed in a Claisen flask with a Widmer-type fractionator (45 cm) fixed thereto. Vacuum distillation was performed. After distilling off the initial distillate fractions in an amount of 6 wt. % based on the amount of materials used, the main distillate was distilled off. The yield of the main distillate was 91 wt. %. The main distillate was subjected to steam distillation at 140° C. and 1.1 KPa, giving the unsaturated alcohol mixture below. The amount of steam blown was 2 wt. % based on water.

The following unsaturated alcohol mixture was produced:

| | |
|---|---|
| Iodine value | 90.7 |
| Cloud point | 3.8° C. |
| Composition | |
| C16 | 4.4% |
| C18 | 1.8% |
| C18F1 | 87.6% |
| C18F2 | 2.6% |
| C20F1 | 0.2% |
| Conjugated diene | 3.1% |
| Color (Hazen) | 10 |

Example 31

Example of Lowering a Conjugated Diene Content to 1 wt. % by Slight Hydrogenation A 5-liter volume electromagnetic agitation type autoclave was provided with 1500 g of the unsaturated alcohol mixture prepared in Example 1, and 2.3 g of a copper-chrome-manganese-barium oxide catalyst (product of Sakai Chemical Co., Ltd., trade name "C-900"). The air inside the system was replaced with hydrogen and a reaction was carried out at 150 to 160° C., and a hydrogen pressure of 0.1 to 0.2 MPa for two hours. After cooling, the catalyst was filtered off.

The residue (1000 g) was placed in a Claisen flask with a Widmer-type fractionator (45 cm) fixed thereto. Vacuum distillation was performed. After distilling off the initial distillate fractions in an amount of 6 wt. % based on the amount of materials used, the main distillate was distilled off. The yield of the main distillate was 91 wt. %. The main distillate was subjected to steam distillation at 140° C. and 1.1 KPa, whereby the following unsaturated alcohol mixture was produced. The amount of steam blown in this operation was 2 wt. % based on water.

Thereby the following unsaturated alcohol mixture was produced:

| | |
|---|---|
| Iodine value | 91.0 |
| Cloud point | 3.7° C. |
| Composition | |
| C16 | 4.8% |
| C18 | 1.9% |
| C18F1 | 89.6% |
| C18F2 | 2.8% |
| C20F1 | 0.1% |
| Conjugated diene | 0.8% |
| Color (Hazen) | 10 |

<Long Term Light Resistance>

The unsaturated alcohol mixture prepared in Example 1 (containing 6.4 wt. % of conjugated diene compound), the unsaturated alcohol mixture prepared in Example 29 (containing 3.0 wt. % of conjugated diene compound), the unsaturated alcohol mixture prepared in Example 30 (containing 3.1 wt. % of conjugated diene compound), the unsaturated alcohol mixture prepared in Example 31 (containing 0.8 wt. % of conjugated diene compound), the unsaturated alcohol mixture prepared in Example 2 (containing 0.1 wt. % of conjugated diene compound) and the unsaturated alcohol mixture prepared in Example 4 (containing 0.1 wt. % of conjugated diene compound) were separately placed in 4 cm-diameter, 10 cm-height glass containers with a lid, exposed to sunlight outdoors for 2 months and inspected for coloring.

The unsaturated alcohol mixtures prepared in Examples 1, 29, 30, 31, 2 and 4 had a color (Hazen) of less than 10 immediately after production. After 2-months exposure to sunlight, the unsaturated alcohol mixture of Example 1 had a color (Hazen) of 50, the unsaturated alcohol mixtures of Examples 29 and 30 showed a color (Hazen) of 40, the unsaturated alcohol mixture of Example 31 had a color (Hazen) of 15, and the unsaturated alcohol mixtures of Examples 2 and 4 showed a color (Hazen) of 10. These results indicate that the long-term light resistance can not be markedly increased by executing distillation and/or steam deodorization after lowering the conjugated diene content to about 3 wt. %, but can be significantly increased by executing distillation and/or steam deodorization after lowering the conjugated diene content to 1 wt. % or less.

INDUSTRIAL APPLICABILITY OF THE INVENTION

According to the invention, there is provided liquid vegetable unsaturated alcohol mixture with excellent liquidity retention that is unlikely to undergo cloudiness despite temperature change, and a process for preparing the same. Further, according to the invention, there is provided a liquid vegetable unsaturated alcohol mixture which has excellent liquidity retention, is unlikely to cause cloudiness despite temperature change, and has superior long-term light resistance of color and color stability in the presence of acidic or basic substances, and a process for preparing the same.

This means that the unsaturated alcohol mixture of the invention can be suitably used as the material for cosmetics (for personal care products).

What is claimed:

1. A process for preparing a liquid vegetable unsaturated alcohol mixture, the process comprising the step of reducing a vegetable unsaturated fatty acid mixture and/or an alkyl ester thereof in the presence of a zinc-type catalyst having a copper content of 30 ppm or less, the vegetable unsaturated fatty acid mixture being prepared from at least one vegetable oil selected from the group consisting of palm oil, coconut oil and palm kernel oil and the step of hydrogenating the obtained liquid vegetable unsaturated alcohol mixture such that the conjugated diene content of the obtained liquid vegetable unsaturated alcohol mixture is lowered without decreasing the iodine value or increasing the cloud point of the obtained liquid vegetable unsaturated alcohol mixture to give a mixture having a conjugated diene compound content of 1 wt. % or less.

2. The process according to claim 1, wherein the zinc-type catalyst is at least one catalyst selected from the group consisting of zinc-chrome oxide, zinc-aluminum oxide, zinc-aluminum-chrome oxide, zinc-chrome-manganese oxide, zinc-iron oxide and zinc-iron-aluminum oxide.

3. The process according to claim 1, wherein the hydrogenation is carried out using a copper-containing catalyst.

4. The process according to claim 1, wherein the hydrogenation is carried out at a hydrogen pressure within the range of from 1 MPa to atmospheric pressure, and a temperature at 50 to 200° C.

5. The process according to claim 1 which includes a step of deodorizing the obtained liquid vegetable unsaturated alcohol mixture.

6. The process according to claim 5, wherein the deodorization is conducted by steam at 100 to 200° C., and 0.1 to 70 KPa with a steam blowing amount of 0.1 to 20 wt.%.

7. The process according to claim 1 which includes a step of distillation.

* * * * *